United States Patent [19]
Tu et al.

[11] Patent Number: 5,891,138
[45] Date of Patent: Apr. 6, 1999

[54] CATHETER SYSTEM HAVING PARALLEL ELECTRODES

[75] Inventors: Hosheng Tu, Tustin; Weng-Kwen Raymond Chia, Irvine, both of Calif.

[73] Assignee: Irvine Biomedical, Inc., Irvine, Calif.

[21] Appl. No.: 909,379

[22] Filed: Aug. 11, 1997

[51] Int. Cl.⁶ .................. A61B 17/39; A61B 5/042; A61N 1/05
[52] U.S. Cl. ............... 606/41; 606/49; 600/374; 607/99; 607/122
[58] Field of Search ............... 600/374; 606/41, 606/49; 607/99, 122

[56] References Cited

U.S. PATENT DOCUMENTS

| | | | |
|---|---|---|---|
| 5,083,565 | 1/1992 | Parins | 600/374 |
| 5,190,050 | 3/1993 | Nitzsche | 128/772 |
| 5,228,442 | 7/1993 | Imran | 128/642 |
| 5,231,995 | 8/1993 | Desai | 128/784 |
| 5,255,679 | 10/1993 | Imran | 128/642 |
| 5,279,299 | 1/1994 | Imran | 128/642 |
| 5,313,943 | 5/1994 | Houser et al. | 600/374 |
| 5,324,284 | 6/1994 | Imran | 606/15 |
| 5,357,956 | 10/1994 | Nardella | 128/642 |
| 5,368,564 | 11/1994 | Savage | 604/95 |
| 5,403,311 | 4/1995 | Abele et al. | 606/49 |
| 5,536,267 | 7/1996 | Edwards et al. | 606/41 |
| 5,551,426 | 9/1996 | Hummel et al. | 600/374 |

FOREIGN PATENT DOCUMENTS

| | | | |
|---|---|---|---|
| 2560052 | 8/1985 | France | 606/41 |

*Primary Examiner*—Lee Cohen

[57] ABSTRACT

A catheter system comprising a delivery catheter with distal and proximal ends; a handle attached to the proximal end of the delivery catheter; the delivery catheter having an electrode deployment means where said electrode deployment means includes a retractable tip section comprising a plurality of deployable parallel electrodes. The tip section has a non-deployed state when it is positioned in the delivery catheter. On the other hand, the tip section has a distended deployed state when it is advanced out of the distal end of said delivery catheter; wherein the deployed electrodes on the tip section has a preformed shape in a parallel manner. This catheter is particularly useful for treating the patient having tachycardia as a result of its more effective electrodes arrangement for intimate tissue contact.

9 Claims, 5 Drawing Sheets

५,८९१,१३८

CATHETER SYSTEM HAVING PARALLEL ELECTRODES

FIELD OF THE INVENTION

The present invention generally relates to improved constructions for a catheter system. More particularly, this invention relates to catheters and methods for mapping and ablating cardiac tissues via a steerable catheter having a plurality of parallel electrodes at its tip section.

BACKGROUND OF THE INVENTION

Symptoms of abnormal heart rhythms are generally referred to as cardiac arrhythmias, with an abnormally rapid rhythm being referred to as a tachycardia. The present invention is concerned with the treatment of tachycardias which are frequently caused by the presence of an "arrhythmogenic site" or "accessory atrioventricular pathway" close to the inner surface of the chambers of a heart. The heart includes a number of normal pathways which are responsible for the propagation of electrical signals from upper to lower chamber necessary for performing normal systole and diastole function. The presence of arrhythmogenic site or accessory pathway can bypass or short circuit the normal pathway, potentially resulting in very rapid heart contractions, referred to here as tachycardias.

Treatment of tachycardias may be accomplished by a variety of approaches, including drugs, surgery, implantable pacemakers/defibrillators, and catheter ablation. While drugs may be the treatment of choice for many patients, they only mask the symptoms and do not cure the underlying causes. Implantable devices only correct the arrhythmia after it occurs. Surgical and catheter-based treatments, in contrast, will actually cure the problem, usually by ablating the abnormal arrhythmogenic tissue or accessory pathway responsible for the tachycardia. It is important for a physician to accurately steer the catheter to the exact site for ablation. Once at the site, it is important for a physician to control the emission of energy to ablate the tissue within the heart.

Of particular interest to the present invention are radiofrequency (RF) ablation protocols which have proven to be highly effective in tachycardia treatment while exposing a patient to minimal side effects and risks. Radiofrequency catheter ablation is generally performed after conducting an initial mapping study where the locations of the arrhythmogenic site and/or accessory pathway are determined. After a mapping study, an ablation catheter is usually introduced to the target heart chamber and is manipulated so that the ablation tip electrode lies exactly at the target tissue site. Radiofrequency energy or other suitable energy is then applied through the tip electrode to the cardiac tissue in order to ablate the tissue of arrhythmogenic site or the accessory pathway. By successfully destroying that tissue, the abnormal signal patterns responsible for the tachycardia may be eliminated.

The tip section of a catheter is referred to herein as the portion of that catheter shaft containing at least one electrode. In one embodiment, a catheter utilized in the endocardial mapping and/or radiofrequency ablation is inserted into a major vein or artery, usually in the neck or groin area. The catheter is then guided into an appropriate chamber of the heart by appropriate manipulation through the vein or artery. The tip of a catheter must be manipulatable by a physician from the proximal end of the catheter, so that the electrodes at the tip section can be positioned against the tissue site to be mapped or ablated. The catheter must have a great deal of flexibility in order to follow the pathway of major blood vessels into the heart. It must permit user manipulation of the tip even when the catheter body is in a curved and/or twisted configuration.

The tip section of a conventional electrophysiology catheter that is deflectable usually contains a plurality of electrodes in series. Several regions of the endocardial surface are relatively rough. When the tip section of a catheter is placed against the endocardial surface, some electrodes on the catheter shaft at the tip section do not contact the endocardial surface. Instead, portion of the catheter shaft at the tip section lies at the ridge of the trabecula. It is one object of the present invention to have a plurality of electrodes not in series on the tip section of a catheter to improve the electrodes contact.

Therefore, while an electrophysiology procedure using an existing catheter has had promising results, the tip section of a known catheter usually has a plurality of electrodes in series. There is a clinical need for an improved catheter and methods comprising a plurality of parallel electrodes for making an intimate contact of the electrode with the target tissues.

SUMMARY OF THE INVENTION

In general, it is an object of the present invention to provide an improved catheter for intimate contact with the target tissues. It is another object of the invention to provide a catheter system with a tip section having a plurality of parallel electrodes. It is another object of the invention to provide a catheter having a plurality of parallel electrodes to be used in effectively mapping the arrhythmogenic points of a patient and/or subsequent ablation. This catheter is particularly useful for treating the patient having tachycardia as a result of its more effective electrodes arrangement for intimate tissue contact.

In one embodiment, a catheter system has a delivery catheter with distal and proximal ends wherein a plurality of primary flat wires is located within the lumen of said delivery catheter. A handle is attached to the proximal end of the delivery catheter. In one embodiment, the plurality of primary flat wire is enclosed within the lumen of a plastic tubing which is within the lumen of said delivery catheter. The primary flat wire is made of a conductive material, such as stainless steel and has a cross-sectional shape and stiffness sufficient to add mechanical strength when advancing the primary flat wires out of the delivery catheter. The primary flat wire in this invention can be any wire, including high strength wire, which is insulated. In a further embodiment, said insulated primary flat wire serves as a conducting means for the electrodes to be connected to an external RF generator for RF energy transmission or to an EKG monitor for mapping. The proximal end of said primary flat wire is attached to a push-pull mechanism on the handle.

The delivery catheter has an electrode deployment means. The electrode deployment means includes a retractable tip section, which constitutes the distal part of said plurality of primary flat wires, comprising a plurality of deployable electrodes each on an individual primary flat wire. In one embodiment, the deployable electrode is a cap electrode secured on an electrode support selected from the group of springs, coils, flat wires, wires, and the like. In one embodiment, the electrode support that is made of a conductive material, is coated with an insulating material. In another embodiment, the electrode support is made of a non-conductive material. In this special case, a conducting wire is provided to transmit electrical signal and/or energy from the cap electrode to an external EKG monitor and/or an RF generator. In either case, said electrode support is, in turn, firmly secured on one of said primary flat wires of that retractable tip section.

The cap electrode along with its electrode support, lies essentially perpendicular to its respective primary flat wire under deployed state. The plurality of electrodes of this invention forms an array of parallel electrodes. Under the non-deployed state, each cap electrode along with its electrode support, lies essentially parallel to the primary flat wires within the delivery catheter. In another particular embodiment, the material for the electrodes may consist of conductive metals such as platinum, iridium, gold, silver, stainless steel, Nitinol, or an alloy of their mixture.

In a further embodiment, the cap electrode is a needle electrode which has a sharp end like a needle. In a still further embodiment, the cap electrode is a multiple-needle electrode which has a plurality of sharp ends. In general, the sharp end has a conductive surface for electrical conductivity and/or RF energy delivery while the remaining portion of said electrodes may have insulative body or insulative surface coating. The tip section has a non-deployed state when it is positioned within the delivery catheter. This non-deployed state is maintained during the catheter system insertion operation into a patient and during withdrawal of the system from a patient.

The tip section has a distended deployed state when it is advanced out of the distal end of said delivery catheter. Deployment of the tip section is accomplished by a pushing action on the push-pull mechanism at the handle. Each cap electrode of the deployed tip section has a preformed shape in relation to its respective primary flat wire so that each electrode, along with the electrode support, would extend outwardly and essentially perpendicular to the outer side of the delivery catheter when deployed. The outer side of said delivery catheter becomes apparent when the steerable catheter system is deflected, whereas the outer side is the side of the catheter system contacting the target tissue. The degree of deployment is controlled by the pushing action at the push-pull mechanism on the handle and is generally completely deployed when the inserted catheter system is ready for mapping or ablation operations inside the chamber of the heart.

The deployed electrodes define the target region for mapping and/or ablation. The tip of each cap electrode is positioned at the target tissue. In an alternate embodiment, the force from the cap electrode onto the electrode support is to make the tissue contact more firmly even under the heart pumping movement. The retraction operation of the tip section is accomplished by pushing down the delivery catheter relative to the tip section of said primary flat wire so that the plurality of cap electrodes lies almost parallel to the primary flat wire within the delivery catheter. The degree of easiness of the retraction is mainly affected by the type or style of the electrode support to the cap electrode.

An insulated conducting wire which is secured to the proximal end of each primary flat wire passes through the interior void of the handle and is thereafter secured to a contact pin of the connector at the proximal end of the handle. From there, the conducting wire is connected to an external RF generator for ablation operations or to an EKG monitor for mapping studies.

The catheter system may further comprise a steering mechanism at the handle for controlling the deflection of the distal section of the delivery catheter. In one embodiment, said steering mechanism is to assist the positioning of said deployed electrodes to be at the close proximity of the target tissue. Usually a rotating ring or a secondary push-pull plunger on the handle is employed as an integral part of the steering mechanism. One end of the steering wire is secured at certain point of the tip section of said delivery catheter or of the primary flat wires, which is within the lumen of said delivery catheter. The other end of the steering wire is attached to the steering mechanism at the handle. The steering mechanism on a steerable catheter or device is well-known to those who are skilled in the art.

In an additional embodiment, the catheter system further comprises a temperature sensing and close-loop temperature control mechanism for the cap electrode having a temperature sensor at the tissue contact site of the electrodes. The location of the temperature sensor is preferably in the proximity of the cap end of the electrodes. One end of the insulated temperature sensing wires is secured to the temperature sensor while the other end is connected to an external temperature control mechanism. A thermocouple or thermistor type temperature measuring and control mechanism on a catheter system is well-known to those who are skilled in the art.

The delivery catheter having a tip section under a non-deployed state is inserted into the body through a cut at the artery or vein. After the catheter approaches the target tissue inside the heart, the tip section is deployed by being pushed out of the delivery catheter from a push-pull mechanism at the handle. Once positioned, the plurality of cap electrodes in an essentially parallel array contacts the target tissue intimately for mapping and/or ablation operations. RF energy can be delivered for ablation purpose.

In a further embodiment, the deployable needle or multiple-needle electrodes having sharp ends penetrate into the endocardial tissue and delivers therapeutic energy for improved treatment. Said catheter system having parallel electrodes means will result in optimal ablation efficiency and a desired deep and large lesion, particularly effective for treating atrial fibrillation and the like.

The system and methods of the present invention have several significant advantages over known catheter apparatus and methods. In particular, a set of parallel electrodes of the delivery catheter of this invention results in a more accurate and more intimate means for mapping and/or ablation capabilities.

BRIEF DESCRIPTION OF THE DRAWINGS

Additional objects and features of the present invention will become more apparent and the invention itself will be best understood from the following Detailed Description of the Exemplary Embodiments, when read with reference to the accompanying drawings.

DETAILED DESCRIPTION OF THE EXEMPLARY EMBODIMENTS

Figure 1:
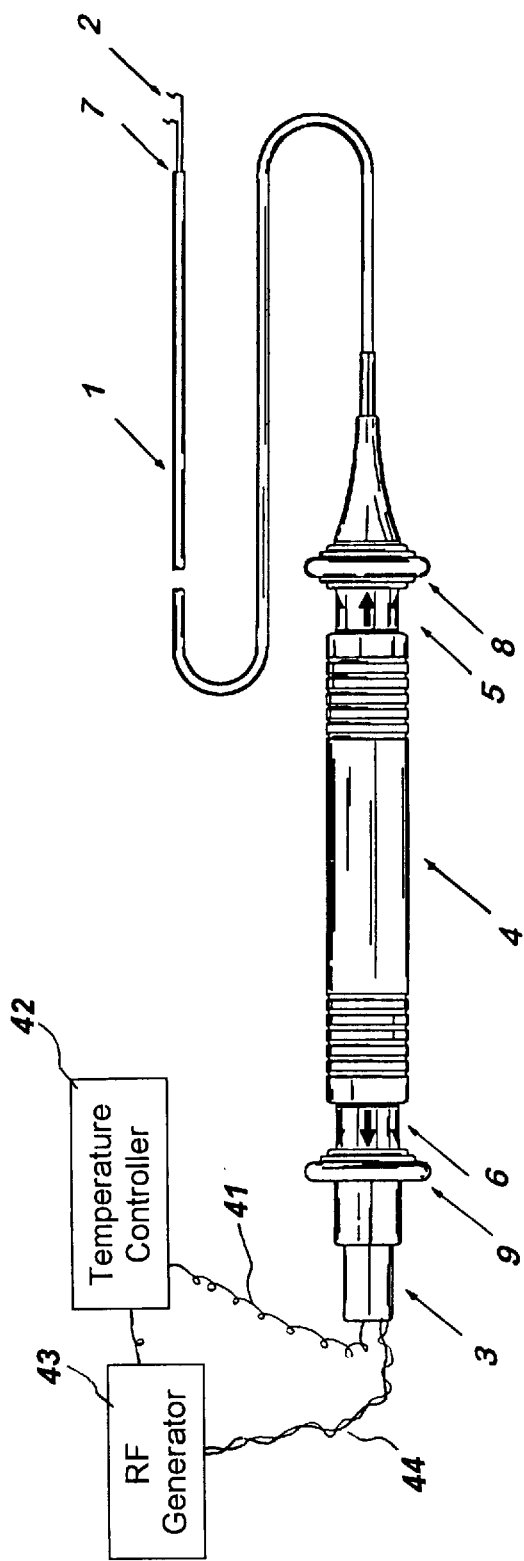
FIG. 1 is an overall view of a catheter system having parallel electrodes at its distal tip section constructed in accordance with the principles of the present invention.

A catheter system constructed in accordance with the principles of the present invention comprises: a delivery catheter with distal and proximal ends, wherein a plurality of primary wires is located within the lumen of said delivery catheter. FIG. 1 shows an overall view of the catheter system 18 having a delivery catheter 1 with a distal end 7 and a proximal end 10. A handle 4 is attached to the proximal end 10 of said catheter 1. The proximal end (not shown) of the plurality of primary flat wires is attached on a push-pull mechanism 5 on the handle 4. A pushing plunger 8 at the push-pull mechanism 5 is used to control the degree of pushing action for tip section 2 deployment. The distal end of said set of primary flat wires comprises an outwardly extended tip section 2 comprising a set of cap electrodes. Each primary flat wire serves as portion of a conducting means for the electrode to be connected to an external RF generator and/or to an EKG monitor. In case a non-conductive means is used to substitute for the primary flat wire function, an insulated conductive wire 44 is to be added for electricity conduction. Said primary flat wire with sufficient stiffness also serves as a mechanical support in advancing the catheter system during insertion operation.

An insulated conducting wire which is secured to the proximal end of each primary flat wire passes through the interior void of the handle 4 and is thereafter secured to a contact pin of the connector 3 at the proximal end of said handle 4. From there, the conducting wire is connected to an external RF generator for ablation operations or to an EKG monitor for mapping studies.

Figure 2:
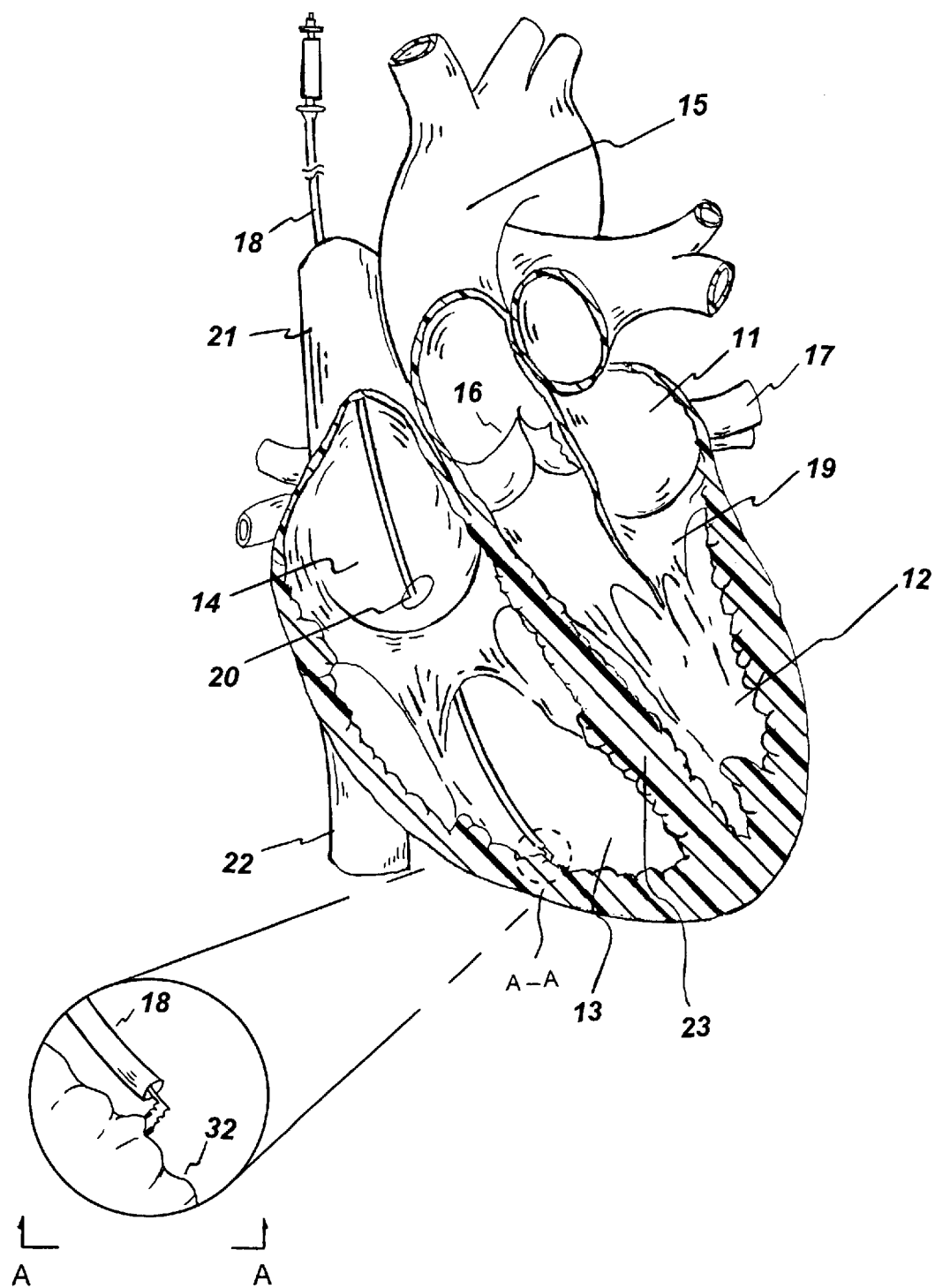
FIG. 2 is a simulated view of a catheter system of this invention inside the chamber of the heart.

FIG. 2 is a simulated view of the placement of the catheter system of this invention inside a chamber of a heart. The heart has a left atrium 11, left ventricle 12, right ventricle 13 and right atrium 14. Aorta 15 connects with left ventricle 12 and contains the aorta valve 16. Pulmonary artery 17 connects with right ventricle 13. Left atrium 11 communicates with left ventricle 12 through mitral valve 19. Right atrium 14 communicates with right ventricle 13 through tricuspid valve 20. Superior vena cava 21 and inferior vena cava 22 lead into right atrium 14. Myocardial wall 23 separates the left and right ventricles. Catheter 18 and the technique of passing it through the heart chambers will be described below. The endocardial surface 32 has many ridges, ripples and/or bumps.

Figure 3:
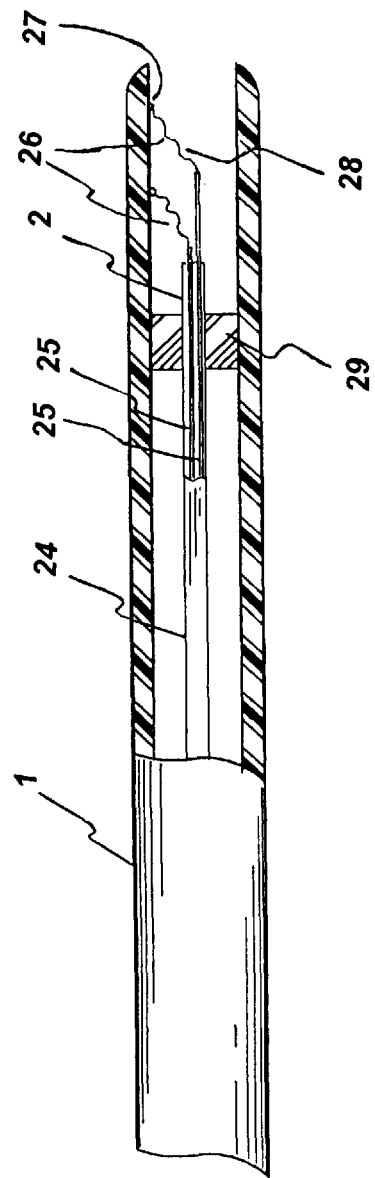
FIG. 3 is a close-up view of the distal section of the catheter system comprising coil supported cap electrodes under non-deployed state.

FIG. 3 is a close-up view of the distal section of the catheter system comprising coil supported cap electrodes in a parallel manner at non-deployed state. The plastic tubing 24, having a retractable tip section 2 and the corresponding plurality of primary flat wires 25, is located within the lumen of the delivery catheter 1. A plurality of deployable electrodes means 26, each comprising a cap electrode 27 and a coiled electrode support 28, constitutes the farther distal end of said tip section 2. The non-deployed state is maintained during system insertion into a patient and system withdrawal from a patient. Under a non-deployed state, the electrodes means 26 of said tip section 2 which have a preformed shape, is held inside the delivery catheter 1. In another alternate embodiment, a coiled electrode support 28 can be substituted by a curved flat wire or a spring.

To prevent blood or body fluid from backflowing into the proximal end of the lumen of the delivery catheter 1, a silicone type check valve 29 is installed at certain opening of the lumen of delivery catheter 1.

In a further embodiment, the catheter system may further comprise a steering mechanism 6 at the handle 4 for controlling the deflection of the distal section of the delivery catheter 1 (FIG. 1). The steering plunger 9 of the steering mechanism 6 at the handle 4 is used to control the degree of deflection of the distal end 7 of the delivery catheter 1. One end of the steering wire is secured at certain distal point of said delivery catheter 1 while the other end is secured to the steering mechanism 6 at the handle 4. The steering mechanism on a steerable catheter is well-known to those who are skilled in the art.

Figure 4:
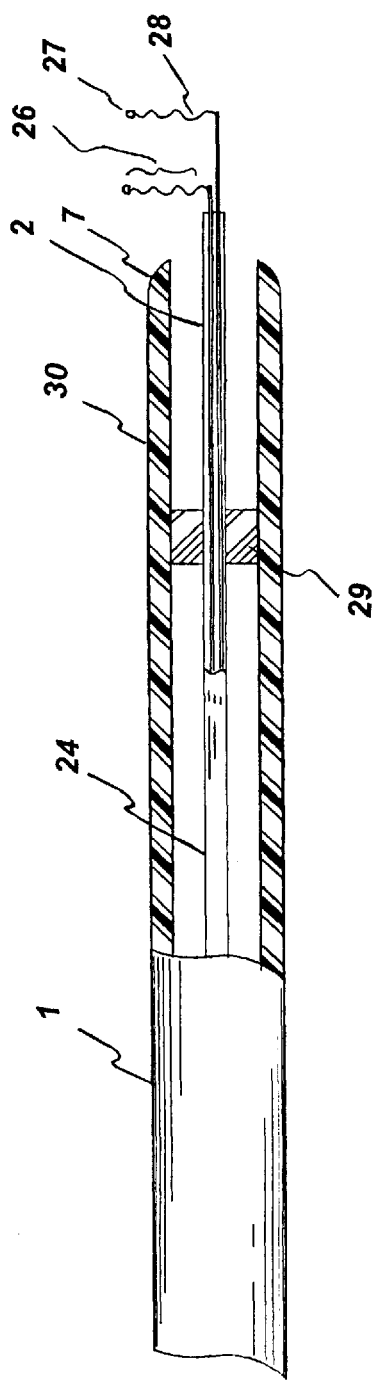
FIG. 4 is a close-up view of the distal section of the catheter system comprising coil supported cap electrodes under deployed state.

FIG. 4 shows a close-up view of said retractable tip section at fully deployed state. The tip section 2 has a distended deployed state when it is advanced out of the distal end 7 of said delivery catheter 1. Deployment of the tip section is accomplished by a pushing action on a push-pull mechanism 5 at the handle 4. Because of its preformed shape of the parallel electrodes, the electrodes means 26 of said distal tip section 2 extends outwardly and essentially perpendicular to the outer side 30 of the delivery catheter 1 when deployed. The cap electrode 27, along with its electrode support 28, lies at an angle relative to or essentially perpendicular to its respective primary flat wire. The plurality of cap electrodes forms an array of parallel electrodes when deployed.

Figure 5:
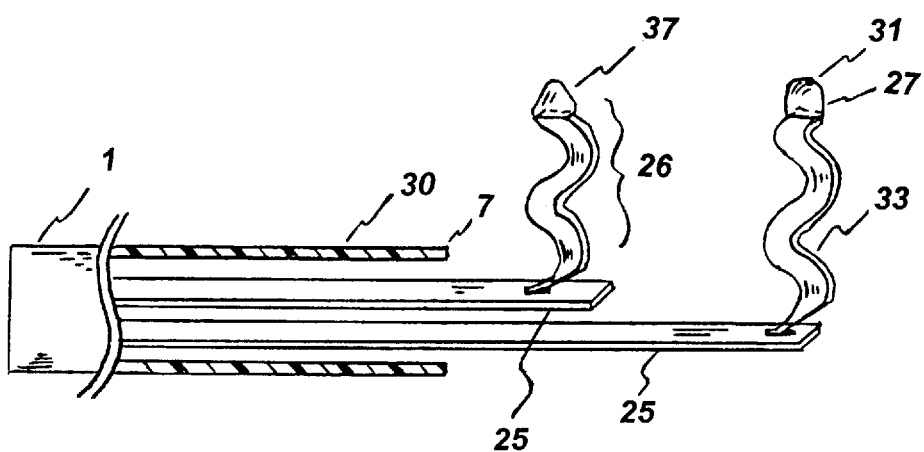
FIG. 5 is a close-up view of an alternate catheter system comprising curved flat wire supported cap electrodes in a parallel manner.

FIG. 5 is a close-up view of an alternate catheter system comprising parallel electrodes supported by a set of curved flat wires. The cap electrode 27, which can be a flat head electrode, a needle electrode 37 or multiple-needle electrode, is secured to a curved flat wire support 33. The curved flat wire support is to provide some resilience for the cap electrode when being pressed against the endocardial tissue. By providing adequate resilience to the cap electrode, the contact between the electrode and the tissue can be maintained intimately even under the systole and diastole movements of the heart. The curved flat wire support 33 is secured to the primary flat wire 25 at a pre-determined angle or close to a perpendicular angle. The extended length of each curved flat wire is so designed that the tip of the cap electrodes are essentially at the same extension level. The electrode support can be selected from the group of springs, coils, meshes, wires, flat wires, curved flat wires, and curved wires.

In an additional embodiment, the catheter system further comprises a temperature sensing and close-loop temperature control mechanism for the electrode having a temperature sensor 31 at the tissue contact site of at least one cap electrode 27. Temperature sensing wires 41 along with a thermocouple or thermistor means is provided to transmit the temperature data from the tissue contact site to an external temperature measuring and control apparatus 42. An algorithm is equipped for the ablation system so that a close-loop temperature control is effective and the temperature data is relayed to an external RF generator 43 for controlled energy delivery.

From the foregoing, it should now be appreciated that an improved catheter system comprising parallel electrodes has been disclosed for tissue mapping and/or ablation procedures. While the invention has been described with reference to a specific embodiment, the description is illustrative of the invention and is not to be construed as limiting the invention. Various modifications and applications may occur to those skilled in the art without departing from the true spirit and scope of the invention as described by the appended claims.

What is claimed is:

1. A catheter system comprising:

a delivery catheter having an outer surface, a distal section, a distal end, a proximal end, and at least one lumen extending between the distal end and the proximal end, wherein a plurality of primary wires is located within the lumen of said delivery catheter, each primary wire has a distal end and a proximal end;

a handle attached to the proximal end of said delivery catheter, the handle having a push-pull mechanism, wherein the proximal ends of the plurality of primary wires are secured to the push-pull mechanism of said handle;

an electrode deployment means positioned at the distal end of said plurality of primary wires, wherein said electrode deployment means includes a retractable tip section, the electrode deployment means comprising a non-deployed state for said retractable tip section when said retractable tip section is positioned in the delivery catheter, and the electrode deployment means further comprising a distended deployed state for said retractable tip section when said retractable tip section is advanced out of the distal end of said delivery catheter;

a plurality of cap electrodes along with their wire supports extended in a parallel manner, each cap electrode being secured to a curved flat wire support, wherein each curved flat wire support is secured to one of the primary wires at a pre-determined angle, and wherein the cap electrodes are deployed by the retractable tip section at a distended deployed state.

2. The catheter system of claim 1, wherein each of the primary wires is a flat wire.

3. The catheter system of claim 2, further comprising a preformed shape for said cap electrodes, wherein the plurality of cap electrodes in a parallel manner on said retractable tip section extends outwardly and essentially perpendicular to the outer surface of the delivery catheter when the electrode deployment means is in a deployed state.

4. The catheter system of claim 3, wherein at least one of the cap electrodes is a needle electrode.

5. The catheter system of claim 4, wherein said needle electrode comprises a distal portion and a proximal portion, the distal portion being made of a conductive material.

6. The catheter system of claim 5, wherein the proximal portion has insulative surface coating.

7. The catheter system of claim 4, further comprising a temperature sensor at close proximity of one of the plurality of cap electrodes and a closed-loop temperature control mechanism for said catheter system, wherein a temperature measured by the temperature sensor is relayed to the closed-loop temperature control mechanism.

8. The catheter system of claim 3, further comprising a steering mechanism at the handle for controlling the deflection of the distal section of said delivery catheter.

9. A method for operating a catheter system inside a body of a patient, the catheter system comprising a delivery catheter having an outer surface, a distal section, a distal end, a proximal end, and at least one lumen extending between the distal end and the proximal end, wherein a plurality of primary wires is located within the lumen of said delivery catheter, each primary wire has a distal end and a proximal end; a handle attached to the proximal end of said delivery catheter, the handle having a push-pull mechanism, wherein the proximal ends of the plurality of primary wires are secured to the push-pull mechanism of said handle; an electrode deployment means positioned at the distal end of said plurality of primary wires, wherein said electrode deployment means includes a retractable tip section, the electrode deployment means comprising a non-deployed state for said retractable tip section when said retractable tip section is positioned in the delivery catheter, and the electrode deployment means further comprising a distended deployed state for said retractable tip section when said retractable tip section is advanced out of the distal end of said delivery catheter; a plurality of cap electrodes along with their wire supports extended in a parallel manner, each cap electrode being secured to a curved flat wire support, wherein each curved flat wire support is secured to one of the primary wires at a pre-determined angle, and wherein the cap electrodes are deployed by the retractable tip section at a distended deployed state; and a RF current generator, wherein an electrical conductor is connected between the RF current generator and each cap electrode; the method comprising the steps of:

introducing the delivery catheter having the distal section under a non-deployed state into the body of a patient through a cut at an artery or vein;

once inside the body, deploying the retractable tip section by operating the push-pull mechanism at the handle;

once positioned, deploying the plurality of cap electrodes along with their wire supports in an essentially parallel array; and conducting an ablation procedure using RF current from the RF current generator.

* * * * *